United States Patent
Ragsdale

(10) Patent No.: US 6,713,292 B2
(45) Date of Patent: Mar. 30, 2004

(54) ELECTROPORATION CUVETTE INSERT FOR FACILITATING MEMBRANE-BASED FUSION

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 10/313,958

(22) Filed: Dec. 6, 2002

(65) Prior Publication Data

US 2003/0124713 A1 Jul. 3, 2003

Related U.S. Application Data

(60) Provisional application No. 60/337,097, filed on Dec. 6, 2001.

(51) Int. Cl.[7] .............................. C12N 13/00; C12M 1/42
(52) U.S. Cl. .................................. 435/173.6; 435/285.2
(58) Field of Search ........................... 435/285.2, 173.6, 435/450, 449, 453, 454; 204/547, 643

(56) References Cited

U.S. PATENT DOCUMENTS 6,150,148 A * 11/2000 Nanda et al. ............ 435/173.6
6,221,665 B1   4/2001 Jaroszeski et al.

* cited by examiner

Primary Examiner—David A. Redding
(74) Attorney, Agent, or Firm—Gerald T. Gray; Townsend and Townsend and Crew LLP

(57) ABSTRACT

Cuvette inserts adapted and configured to fit within an electroporation cuvette. The inserts each include a support structure that holds a porous membrane. When positioned within the cuvette, the membrane is positioned proximal the cuvette electrodes to facilitate membrane-based fusion of cells. In certain aspects, a tube extends through the support structure to allow for application of negative pressure in a convenient location away from electrode contacts and other components of the cuvette or cuvette holder.

14 Claims, 1 Drawing Sheet

ELECTROPORATION CUVETTE INSERT FOR FACILITATING MEMBRANE-BASED FUSION

CROSS-REFERENCES TO RELATED APPLICATIONS

This application claims the benefit of U.S. Provisional Patent Application Serial No. 60/337,097, titled "ELECTROPORATION CUVETTE INSERT FOR FACILITATING MEMBRANE-BASED FUSION", filed Dec. 6, 2001, which is hereby incorporated by reference in its entirety.

BACKGROUND OF THE INVENTION

The present invention relates generally to electro-fusion and electroporation systems, and more particularly to devices that allow for electro-fusion experiments to be conducted using electroporation systems and devices.

It is well known to fuse cells using a membrane suspended between parallel electrodes. U.S. Pat. No. 6,221,665, which is hereby incorporated by reference for all purposes, discloses one such system for performing cell-cell electrofusion. In the disclosed system, a gentle vacuum is drawn from below a membrane which causes the cells to be sucked-down into the membrane. As shown in FIG. 1, a vacuum is created in the region 10 below the membrane 20 using, e.g., a syringe 30 or other vacuum generating device. A potential is then applied to the electrodes, and the membranes of adjacent cells are disrupted. The cell machinery reconstitutes the adjacent membrane such that they become contiguous. This causes fusion but without need for the AC currents to cause dielectrophoresis (movement of the cells in a special electric field such that the membranes of the cells are adjacent) as is the usual method.

It would be advantageous to implement such a fusion system in an electroporation system, for example, to use the DC source of the electroporation system. However, such a fusion system as described above would not be useful in a typical electroporation cuvette system arrangement as the area in which the vacuum port is located is in the same area of electrical contact to the cuvette electrodes. Hence, it would be desirable to provide a simple and efficient means of creating a fusion cuvette from a standard electroporation cuvette without interfering with the electrode contact area.

BRIEF SUMMARY OF THE INVENTION

The present invention provides cuvette inserts adapted and configured to fit within an electroporation cuvette. The inserts each include a support structure that holds a porous membrane. When positioned within the cuvette, the membrane is positioned proximal the cuvette electrodes to facilitate membrane-based fusion of cells. In certain aspects, a tube extends through the support structure to allow for application of negative pressure in a convenient location away from electrode contacts and other components of the cuvette or cuvette holder.

According to an aspect of the invention, an electroporation cuvette insert for creating a membrane-based fusion cuvette from an electroporation cuvette is provided. The insert typically includes a porous membrane having an upper surface and a lower surface, a support structure for holding the membrane, the support structure being of a sufficient dimension to securely match, or fit within, the inner walls of an electroporation cuvette, wherein the support structure creates a substantially sealed chamber within the cuvette below the lower surface of the membrane when inserted into the cuvette. the insert also typically includes a tube extending upwards relative to the upper surface of the membrane and through the support structure, wherein when a negative pressure is applied to a distal end of the tube, a negative pressure is created in the sealed chamber of the cuvette, thereby creating a pressure gradient at the upper surface of the porous membrane.

According to another aspect of the invention, an electroporation cuvette insert is provided in combination with an electroporation cuvette. The insert typically includes a porous membrane having an upper surface and a lower surface, a support structure for holding the membrane, the support structure being of a sufficient dimension to securely fit within the inner walls of the electroporation cuvette, wherein the support structure creates a substantially sealed chamber within the cuvette below the lower surface of the membrane when inserted into the cuvette. the insert also typically includes a tube extending upwards relative to the upper surface of the membrane and through the support structure, wherein when a negative pressure is applied to a distal end of the tube, a negative pressure is created in the sealed chamber of the cuvette, thereby creating a pressure gradient at the upper surface of the porous membrane.

According to yet another aspect of the present invention, a method is provided for forming a fusion-based cuvette from an electroporation cuvette. The method typically includes providing an electroporation cuvette having external electrode contacts proximal a bottom portion, providing an insert having a support structure for holding a porous membrane, and a tube extending through the support structure, the insert being configured to fit within the electroporation cuvette, and securing the insert within the electroporation cuvette so as to form a substantially air-tight chamber below the support structure and membrane, and such that application of a vacuum to the end of the tube creates a negative pressure in the chamber and a pressure gradient at an upper surface of the membrane.

Reference to the remaining portions of the specification, including the drawings claims and Appendices, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

Figure 1:
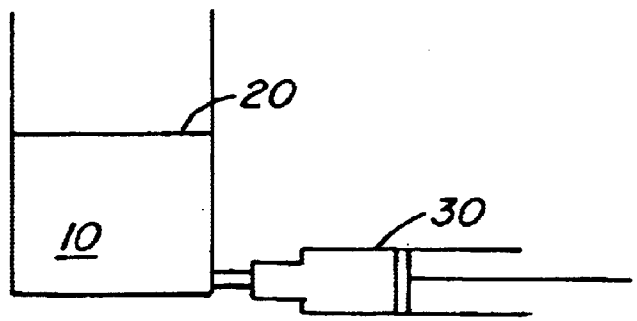
FIG. 1 illustrates an electrofusion chamber according to a prior system.
Figure 2:
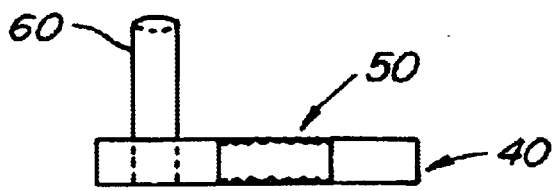
FIG. 2 illustrates a cuvette insert according to an embodiment of the present invention.
Figure 3:
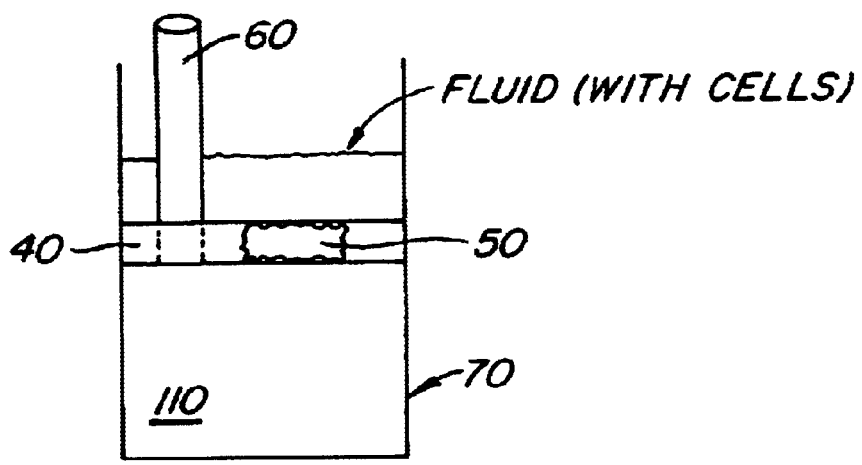
FIG. 3 illustrates an insert in a cuvette according to an embodiment of the present invention.

FIG. 2 illustrates an insert 40, according to an embodiment of the present invention, which can be placed in an electroporation cuvette, e.g., between the cuvette electrodes. The insert includes a membrane region 50 and also contains a snorkel tube 60. When placed within an electroporation cuvette 70 as shown in FIG. 3, the snorkel tube 60 preferably rises above the cuvette in a region which does not interfere with any of the electrodes or other cuvette components (except perhaps the cuvette cover). A flexible tube connection can be provided to the tube (or directly to an opening in the insert) with a further connection to a vacuum generating device (e.g., vacuum pump) for generating a negative pressure.

The cells to be fused are placed in the cuvette along with the electroporation media. The vacuum device preferably operates from the top of the cuvette and generates a negative pressure below the membrane region 110 which draws the cells down against the membrane. The electroporation voltage may then be applied to the electrodes (not shown). Cells are released by removing the vacuum.

The insert 40 preferably includes a simple molded part (e.g., a single integral plastic mold structure). Tube 60 may be attached as a separate operation (e.g., insertion of tube 60 into an orifice created during the formation of insert 40) or as part of the formation of the insert (e.g., molding, extruding or machining using a nonconductive material such as plastic). The membrane is preferably attached after formation of the insert structure as is well known. In one embodiment, the insert is bonded into a standard cuvette. For example, the insert may be glued or attached to the inner walls of a cuvette using an epoxy, adhesive or other attaching compound or material. In another embodiment, a special molded cuvette is provided that allows snapping-in or easier bonding of the insert in-place so as to securely fasten the insert within the cuvette. A lip may be provided within the inner walls of the cuvette that allows the insert to rest thereon. The chamber created by the insert below the substrate/membrane should be substantially air-tight so as to create a sufficient negative pressure gradient at the membrane 50 when a vacuum is applied at the snorkel tube end.

It should be appreciated that the geometry of an insert according to the present invention may vary. For example, different insert geometries may be produced to allow for different spacings of electrodes, different cuvette geometries and/or various experiments as desired. Additionally, the size and dimensions of the membrane region 50 may vary as desired for the particular application. The membrane may include a mesh, a porous membrane or other porous material, and the pore size and number of pores per unit area can be adjusted, depending on the cell type under investigation. Further, in certain aspects, two or more electrodes may be deposited on the insert, for electrically contacting the electrodes of the cuvette, where more localized fields are desired. For example, ends of deposited electrodes may be positioned proximal the membrane or within the membrane to provide localized fields to the cells in the membrane.

Thus, the inserts of the present invention advantageously provide, inter alia:

(1) means to allow membrane-based fusion in a standard electroporation cuvette.

(2) means to draw a vacuum from a location, e.g., the top of the cuvette, at which there are fewer interfering structures.

(3) adaptability, e.g., different inserts for different spacings of electrodes.

(4) ease of use, e.g., snap-in inserts for special cuvettes.

Additionally, the inserts of the present invention are particularly useful in the automated electroporation systems and electroporation cuvettes as disclosed in copending U.S. patent application Ser. No. 10/313,893, filed on even date herewith, claiming priority to U.S. Provisional Patent Application Serial No. 60/337,095, filed Dec. 6, 2001, both titled "AUTOMATIC ELECTROPORATION OPTIMIZATION SYSTEM", the contents of which are both hereby incorporated by reference in their entirety.

Techniques for determining various timing and control parameters for electroporation systems and fusion-based cuvettes as described herein can be found in copending U.S. patent application Ser. No. 10/313,951, filed on even date herewith, claiming priority to U.S. Provisional Patent Application Serial No. 60/337,103, filed Dec. 6, 2001, both titled "RESISTANCE CIRCUIT STABILIZATION AND PULSE DURATION CONTROL SYSTEMS FOR ELECTROPORATION INSTRUMENTS", the contents of which are both hereby incorporated by reference in their entirety.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, although application of a DC current to the electrodes is preferred in some aspects, it should be understood that current or voltage signals having a variety of waveforms, such as for example, exponential waveforms, square waves, triangular waves, sinusoidal waves, and any combination of different waveshapes, may be utilized. Therefore, the scope of the appended claims should be accorded the broadest interpretation so as to encompass all such modifications and similar arrangements.

What is claimed is:

1. An electroporation cuvette insert for creating a membrane-based fusion cuvette from an electroporation cuvette, the insert comprising:

a porous membrane having an upper surface and a lower surface;

a support structure for holding the membrane, the support structure being of a sufficient dimension to securely match the inner walls of an electroporation cuvette, wherein the support structure creates a substantially sealed chamber within the cuvette below the lower surface of the membrane when inserted into the cuvette; and a tube extending upwards relative to the upper surface of the membrane and through the support structure, wherein when a negative pressure is applied to a distal end of the tube, a negative pressure is created in the sealed chamber of the cuvette, thereby creating a pressure gradient at the upper surface of the porous membrane.

2. The insert of claim 1, wherein the support structure and tube form one integral structure.

3. The insert of claim 1, wherein the tube is a separate piece that attaches to the support structure.

4. An electroporation cuvette insert in combination with an electroporation cuvette, the insert comprising:

a porous membrane having an upper surface and a lower surface;

a support structure for holding the membrane, the support structure being of a sufficient dimension to securely fit within the inner walls of the electroporation cuvette, wherein the support structure creates a substantially sealed chamber within the cuvette below the lower surface of the membrane when inserted into the cuvette; and a tube extending upwards relative to the upper surface of the membrane and through the support structure, wherein when a negative pressure is applied to a distal end of the tube, a negative pressure is created in the sealed chamber of the cuvette, thereby creating a pressure gradient at the upper surface of the porous membrane.

5. The insert of claim 4, wherein the support structure and tube form one integral structure.

6. The insert of claim 4, wherein the tube is a separate piece that attaches to the support structure.

7. A method of forming a fusion-based cuvette from an electroporation cuvette, the method comprising:

provinding an electroporation cuvette having external electrode contacts proximal a bottom portion;

providing an insert having a support structure for holding a porous membrane, and a tube extending through the support structure, said insert being configured to fit within the electroporation cuvette;

securing the insert within the electroporation cuvette so as to form a substantially air-tight chamber below the support structure and membrane, and such that application of a vacuum to the end of the tube creates a negative pressure in the chamber and a pressure gradient at an upper surface of the membrane.

8. The method of claim 7, wherein securing includes snapping the insert in place within the cuvette.

9. The method of claim 7, wherein securing includes applying an adhesive to secure the insert in place within the cuvette.

10. The method of claim 7, wherein the tube and insert are separate pieces, and wherein securing includes attaching the tube to an opening in the support structure.

11. The method of claim 7, wherein the tube and insert form one integral structure.

12. The method of claim 7, further including attaching a vacuum source to a distal end of the tube.

13. The method of claim 12, wherein electrodes are proximal the membrane, the method further including generating a negative pressure within the chamber and applying a potential to the electrodes.

14. The method of claim 13, wherein the potential is a DC current.

* * * * *